United States Patent [19]
Siegfried et al.

[11] Patent Number: 5,833,961
[45] Date of Patent: Nov. 10, 1998

[54] POLYESTER-BASED SUNCREEN FORMULATIONS

[75] Inventors: Robert W. Siegfried, Medford; Anna Marie Howe, Ewing; Rocco V. Burgo, Jr., Cherry Hill, all of N.J.; Andrew Peter O'Connor, Drexel Hill, Pa.; Thomas Grebenar, Jr., Ewing, N.J.

[73] Assignee: Inolex Investment Corporation, Wilmington, Del.

[21] Appl. No.: 673,707

[22] Filed: Jun. 25, 1996

[51] Int. Cl.⁶ .............................. A61K 7/42; A61K 7/00; A61K 31/74

[52] U.S. Cl. .................... 424/59; 424/60; 424/78.08; 424/78.17; 424/400; 424/401

[58] Field of Search .............. 424/89, 60, 400, 424/401, 78.08, 78.17

[56] References Cited

U.S. PATENT DOCUMENTS

| | | | |
|---|---|---|---|
| 3,956,401 | 5/1976 | Scardera et al. | 568/625 |
| 3,976,789 | 8/1976 | Tomita et al. | 514/785 |
| 4,450,091 | 5/1984 | Schmolka | 252/174.21 |
| 4,533,545 | 8/1985 | Sebag | 424/70.1 |
| 4,549,009 | 10/1985 | Higaki et al. | 528/301 |
| 4,606,916 | 8/1986 | Hofinger et al. | 424/70.1 |
| 4,671,955 | 6/1987 | Palinczar | 424/47 |
| 4,683,134 | 7/1987 | Palinczar | 424/59 |
| 4,699,779 | 10/1987 | Palinczar | 424/59 |
| 4,708,813 | 11/1987 | Snyder | 252/90 |
| 4,710,371 | 12/1987 | Palinczar | 424/47 |
| 4,731,242 | 3/1988 | Palinczar | 424/59 |
| 4,853,430 | 8/1989 | Stühler et al. | 524/604 |
| 4,904,524 | 2/1990 | Yoh | 424/401 |
| 4,943,624 | 7/1990 | Regen | 528/301 |
| 4,950,475 | 8/1990 | Vishnupad et al. | 424/83 |
| 4,978,526 | 12/1990 | Gesslein et al. | 424/70.1 |
| 5,017,365 | 5/1991 | Niedbala | 424/59 |
| 5,164,471 | 11/1992 | O'Lenick, Jr. | 528/26 |
| 5,210,133 | 5/1993 | O'Lenick, Jr. | 525/54.1 |
| 5,219,558 | 6/1993 | Woodin, Jr. et al. | 424/59 |
| 5,242,433 | 9/1993 | Smith et al. | 604/289 |
| 5,254,109 | 10/1993 | Smith et al. | 604/289 |
| 5,368,581 | 11/1994 | Smith et al. | 604/290 |
| 5,417,674 | 5/1995 | Smith et al. | 604/289 |

FOREIGN PATENT DOCUMENTS

| | | |
|---|---|---|
| 0 229 400 A2 | 7/1987 | European Pat. Off. . |
| 0 551 749 A2 | 7/1993 | European Pat. Off. . |
| 1 426 289 | 12/1965 | France . |
| Wo 96/06878 | 3/1996 | WIPO . |

OTHER PUBLICATIONS

Inolex® Chemical Company, "Water Resistant Sunscreen 383–208 MA–1", one page (1994).

Inolex® Chemical Company, "Sunscreen Water Resistant/Substantivity", pp. 1–7 (1994).

*Primary Examiner*—Shelley A. Dodson
*Attorney, Agent, or Firm*—Panitch Schwarze Jacobs & Nadel, P.C.

[57] ABSTRACT

Sunscreen formulations including functionalized polyesters and at least two organic active sunscreen ingredients are provided. One of the organic active ingredients is at least partially soluble in the other, and the organic active ingredients are compatible and co-soluble with the functionalized polyester. The functionalized polyesters are also included in sunscreen formulations as dispersing agents for inorganic active sunscreen ingredients.

21 Claims, 1 Drawing Sheet

Fig. 1

POLYESTER-BASED SUNCREEN FORMULATIONS

FIELD OF THE INVENTION

The present invention relates to the field of polyester-based sunscreen formulations and sunscreen formulations including polyester dispersing agents for inorganic active sunscreen ingredients.

BACKGROUND OF THE INVENTION

The public concern over the risks of skin cancer and premature skin aging due to sun exposure has grown in recent years. In response to these public concerns, consumer use of topical products which afford protection from the sun's harmful rays is increasing. In addition to purchasing products which offer protection from ultraviolet (UV) radiation during outdoor recreational activities, consumers have become more interested in daily use products containing UV-protection, such as moisturizers, foundation make-up and other cosmetic products. Increased concern over skin cancer and photo-aging has also resulted in increased sales of products offering sun-protection factor (SPF) values of at least 15.

Although increased use of UV-protective products helps reduce occurrences of skin cancer, risks associated with exposure to high concentrations of UV-absorbing ingredients must also be considered. Sunscreen products are regulated as drugs, and the list of active ingredients approved for use in sunscreens is accordingly limited. Due to the availability of a limited number of effective active ingredients and the increasing use of high SPF-value daily-use products, consumers daily apply relatively large quantities of active sunscreen ingredients to their skin. This increased level of exposure to UV-absorbing active ingredients, particularly organic ingredients, has become an issue of concern to sunscreen marketers.

Recently, the use of inorganic UV-scattering and absorbing agents has become popular. This trend is primarily due to the concern that high concentrations of organic UV-absorbing materials can be irritating to individuals with sensitive skin. Although inorganic active sunscreen ingredients (such as titanium dioxide and zinc oxide) are generally thought to present little potential for skin irritation or sensitization, it is difficult to achieve high SPF values using these active ingredients alone. To deliver protection, inorganic active ingredients must be adequately dispersed within formulations, must remain dispersed over the shelf life of the product, and must be sufficiently dispersed within the film formed on the surface of the skin following application. Additionally, formulations relying exclusively, or primarily, on inorganic active ingredients are usually not resistant to wash-off following skin contact with water or perspiration and often lack aesthetically acceptable sensory characteristics.

Formulating successful sunscreen products which rely entirely on inorganic active ingredients is challenging. Consequently, most high SPF commercial sunscreen products contain significant concentrations of organic active ingredients.

Currently, the most commonly used organic active ingredient, worldwide, is octyl methoxycinnamate (OMC). OMC protects both within the UV-A and UV-B bands of the spectrum. In order to achieve SPF values of at least 15, it is generally believed to be necessary to include an active ingredient with maximum absorption within the UV-A band. In the United States, the most efficient UV-A-absorbing active ingredient permitted for use under the Food and Drug Administration's Tentative Final Monograph for Over-The Counter sunscreen products is benzophenone-3, i.e., oxybenzone. Although OMC is not known to have risks associated with its use, many marketers are concerned that consumer exposure to relatively high concentrations of this active ingredient on a daily basis may eventually result in a segment of the population which becomes sensitized to OMC. It is also believed that individuals with sensitive skin may become increasingly sensitized. Some studies have shown that, in test groups of such users, a certain percentage exhibit an immediate irritation response to products containing even minimal concentrations of OMC.

Safety concerns are much greater with respect to consumer exposure to benzophenone-3. Benzophenones have been reported to produce immediate urticarial reactions and delayed eczematous, photo-allergic and contact-allergic reactions. Through use of a mathematical model, A. Watkinson and collegues have shown a significant amount of benzophenone-3 can penetrate skin and enter systemic circulation. A. Watkinson et al., "Prediction of the Percutaneous Penetration of Ultraviolet Filters in Sunscreen Formulation, *International Journal of Cosmetic Science*, vol. 14, pp. 265–275 (1992). Therefore, daily use of benzophenone-3 also presents concern in the sunscreen field.

Accordingly, there is a need in the art for a sunscreen formulation which provides a sufficient level of SPF protection, but which reduces the risks associated with the daily use of organic active sunscreen ingredients such as OMC and benzophenone-3. There is also a need in the art for a sunscreen formulation which exhibits improved dispersibility of inorganic active sunscreen ingredients in the formulation.

SUMMARY OF THE INVENTION

The present invention includes a sunscreen formulation which is formed from a functionalized polyester, a first organic active sunscreen ingredient and a second organic active sunscreen ingredient. The first ingredient is at least partially soluble in the second ingredient in the formulation.

In one embodiment, the sunscreen formulation includes from about 1 to about 50 parts by weight of a functionalized polyester and from about 50 to about 99 parts by weight combined of the first and second organic active sunscreen ingredients. The polyester is a reaction product of at least one diol, at least one diacid and at least one polyfunctional alcohol or polyfunctional acid present in an amount up to 10% by weight and sufficient to provide a functionality of at least 2 in the functionalized polyester.

The invention also includes a method for reducing the degree of penetration of organic active sunscreen ingredients through the outer stratum corneum layer and for improving the water resistance of a sunscreen formulation. The method includes providing to a sunscreen formulation having a first organic active sunscreen ingredient, a second organic active sunscreen ingredient and a functionalized polyester, wherein the first ingredient is at least partially soluble in the second ingredient in the formulation. In one embodiment, the method includes providing a glycerin/diethylene glycol/adipate crosspolymer as the polyester and octyl methoxycinnamate and benzophenone-3 as the first and second organic active sunscreen ingredients. In this method, the ratio of parts by weight of the benzophenone-3 to parts by weight of the octyl methoxycinnamate in the sunscreen formulation is from about 1:8 to about 1:1.

The invention further includes a sunscreen formulation which includes a dispersion of an inorganic active sunscreen ingredient in a functionalized polyester.

BRIEF DESCRIPTION OF THE DRAWING

The following description of the preferred embodiments of the invention, will be better understood when read in conjunction with the appended drawing. For the purpose of illustrating the invention, there is shown in the drawing a graphical representation which is referred to in the detailed description and which aids in understanding the present invention. It should be understood, however, that the invention is not limited to the embodiment represented in the drawing. In the drawing.

DETAILED DESCRIPTION OF PREFERRED EMBODIMENTS

The organic active-based sunscreen formulations of the present invention show improved resistance to water and perspiration. In addition, they function to fix and hold organic active ingredients in the outer stratum corneum layer of the skin to prevent penetration of the organic active ingredients through the skin. The substantivity aids of the formulation are functionalized polyesters which are compatible with the organic active ingredients and which improve the solubility level of the organic active ingredients in each other. Use of the functionalized polyesters with combinations of particular organic active sunscreen ingredients provides a synergistic effect with respect to the solubility levels of the organic active ingredients. Further, the functionalized polyesters of the present invention are good dispersing agents for use with inorganic active sunscreen ingredients.

Preferred embodiments of the sunscreen formulations will be described first with respect to the organic active sunscreen ingredients and second with respect to the method for reducing the degree of penetration of organic active sunscreen ingredients through the outer stratum corneum layer and for improving the water resistance of a sunscreen formulation. The inorganic active sunscreen ingredient-based formulations will then be described.

The sunscreens of the present invention include a functionalized polyester preferably having a molecular weight of from about 500 to about 20,000. The polyester is a reaction product of at least one linear or branched chain aliphatic dihydric compound having two —OH groups, i.e. at least one diol, and at least one linear or branched chain aliphatic dicarboxylic acid having two —COOH groups, i.e. at least one diacid. The polyester backbone is derived from the co-condensation of such aliphatic diols and diacids. The diol may contain from 2 to 10 ether linkages (—R—O—R—) or tertiary amine groups ($NR_3$).

Preferably, the polyester is functionalized and/or crosslinked by reacting at least one diol, at least one diacid as noted above and at least one polyfunctional acid or polyfunctional alcohol, preferably having a functionality of 3 or greater with respect to —OH or —COOH groups. The polyfunctional acid or alcohol should be provided in an amount sufficient to provide a functionalized polyester having a functionality, either —OH or —COOH, of at least 2. Preferably, the polyfunctional acid or alcohol is provided in an amount of up to about 10% by weight of the reactants.

The resulting polyesters are either hydroxy or acid functional and preferably have either —OH or —COOH terminal end groups which thereby provide a functionality of at least 2. A greater degree of functionality is necessary if a greater degree of crosslinking is provided.

The amount of acid or alcohol to be used, in equivalent weight, is determined in accordance with the number of —OH or —COOH groups, or equivalents, to be provided per unit mass of polymer. The molecular weight of the acid or alcohol can then be used to calculate the appropriate weight percentage of acid or alcohol required to achieve the desired number of equivalents. Preferably, one or less equivalent of acid or alcohol is provided per equivalent desired in the final polymer such that the resulting polymer will have substantially no free acid or alcohol remaining and all of the acid or alcohol will be used in the functionalizing reaction.

The diacids used for forming the polyesters are preferably of from 2 to 20 carbon atoms. Suitable diacids for use in forming the polyesters include, for example, malonic acid, maleic acid, fumaric acid, acetylene dicarboxylic acid, succinic acid, glutaric acid, adipic acid, pentanedioic acid, muconic acid, pimelic acid, suberic acid, azelaic acid, sebacic acid, undecandioic acid, traumatic acid and branched and straight chain alkyl, alkenyl and nonaromatic cycloalkyl and nonaromatic cycloalkenyl derivatives of those acids. Preferably, the acid is adipic acid. One skilled in the art, based on this disclosure, would be aware that such a list of possible diols is exemplary in nature and that other suitable diols having similar properties are within the scope of this disclosure.

Suitable diols for use in forming the polyesters include any alkane diol, alkene diol, alkyne diol, nonaromatic cycloalkane diol or nonaromatic cycloalkene diol. Preferably, such diols have from 2 to 20 carbon atoms. Such diols include, for example, ethylene glycol, propylene glycol, 1,2 butanediol, 1,5-pentanediol, cyclopentanediol, 3,3-dimethyl-1,2-butanediol, 3-hexyne-2,5-diol and the like. These diols are exemplary in nature and it should be understood by one skilled in the art, based on this disclosure, that the position of the —OH group on such diols may be varied. For example, 1,2 pentanediol, 1,3 pentanediol and 1,5 pentanediol are all suitable diols. Further, ether-containing diols having the formula HO—($CH_2$—$CH_2$—O—)$_b$—$CH_2$—$CH_2$—OH, where b is from 1 to 5, may also be used. Preferably, an ether group-containing diol such as diethylene glycol is used to form the polyester of the present invention.

The above diacids and diols may be used singly or in a mixture of diacids and diols. Further, as noted above, when forming the polyesters of the present invention, a polyfunctional acid or polyfunctional alcohol may be added for crosslinking the polyester and/or providing —OH or —COOH functionality. Suitable polyfunctional acids include any polycarboxylic acid having the required functionality as noted above. Suitable polyfunctional alcohols include functionalized alcohols having the required —OH functionality as noted above. Preferably, a polyfunctional alcohol is used to provide crosslinking and/or to form an —OH terminated polyester.

Examples of suitable polyfunctional alcohols include 1,2, 3-propanetriol (glycerin), 1,2,4-butanetriol, 1,1,1,-tris (hydroxymethyl)ethane, 1,2,6-trihydroxyhexane and the like. It will be understood from this disclosure that other polyfunctional alcohols or acids may be used to provide the required functionality and the above examples are not intended to be limiting.

The polyesters may be formed according to any suitable polymerization method. Preferably, the polyesters are formed by co-condensation of the diacids and diols in the presence of the functionalized crosslinking acid or alcohol.

Preferably, the resulting polyesters according to the present invention will have a degree of cross-linking in accordance with its functionality as shown in formula (I) below:

wherein: $R^1$ is independently —O— or —O—$R^2$—O—;
$R^2$ is independently $C_2$–$C_{10}$ aliphatic having 0–5 oxygen atoms as ether groups;
$R^3$ is —O—(C=O)—$R^1$—H, H, or —O—[(C=O)—$R^2$($R^4$)$_m$—(C=O)—O—$R^2$($R^3$)$_n$—O]$_p$—(C=O)—$R^2$($R^4$)$_m$—(C=O)—$R^1$—H;
$R^4$ is —(C=O)—O—$R^1$—H, H, or —(C=O)—O—$R^2$—O[(C=O)—$R^2$($R^4$)$_m$—(C=O)—O—$R^2$($R^3$)$_n$—O]$_p$—(C=O)—$R^2$($R^4$)$_m$(C=O)—$R^1$—H;
m is independently an integer and $1 \leq m \leq 5$;
n is independently an integer and $1 \leq n \leq 5$; and
p is an integer and $3 \leq p \leq 100$.

One hydroxy-terminated polyester according to the above formula (I) useful in the present invention is glycerin/diethylene glycol/adipate crosspolymer (GDGAC), wherein the diol is diethylene glycol, the diacid is adipic acid and the crosslinking polyfunctional alcohol is glycerin. GDGAC is a hydroxy-terminated polyester including repeating units of diethylene glycol and adipic acid randomly cross-linked through the use of glycerin. The average molecular weight is 5,000. The resulting polymer has a structure (II) according to formula (I) as shown below:

where $R^1$ from formula (I) is —O—$R^2$—O—; $R^2$ is independently $(CH_2)_4$ when $R^4$ is H and m is 1 or $(CH_2O)_2$; $R^3$ represents the cross-linked chain as shown where n is 1; and p is varied to adjust molecular weight to achieve an average molecular weight of about 5,000.

In forming suitable functionalized polyesters for use in the present invention, the terminal end groups can be left as is and used in the sunscreen formulation as is the case with formula (I) above, or further end-functionalized by reacting with at least one compound, such as, for example, a linear or branched chain aliphatic monofunctional acid of from about 2 to 40 carbon atoms, a linear or branched chain monofunctional alcohol of from about 2 to 40 carbon atoms or combinations of such acids and alcohols. The polyesters can also be end-functionalized by reacting them with primary or secondary amines or silicon-containing compounds. The amount of the functionalizing reactants provided are determined in accordance with the desired functionality. The number of equivalents per unit mass required to provide the specific functionality for a given application of the functionalized polyester is determined as described above. Based on the number of necessary equivalents per unit mass, the molecular weight of the functionalizing reactant is then used to determine the amount of that reactant to be provided to the reaction to achieve the specific functionality in the resulting polyester. Preferably, as described above, the equivalents are determined such that substantially no functionalizing reactant remains in a free form in the resulting polyester and substantially all of the reactant is used in the functionalizing reaction.

The linear and branched chain aliphatic monofunctional acids may include any carboxylic acid having from 2 to 40 carbon atoms. Examples of such acids include, formic acid, acetic acid, propionic acid, butyric acid, valeric acid, caproic acid, caprylic acid, capric acid, lauric acid, myristic acid, palmitic acid, stearic acid and similar straight chain aliphatic acids. The monofunctional group may be attached at any carbon site along the chain. Alkenyl, alkynyl, branched chain and nonaromatic cyclic acid derivatives of such straight chain acids having the appropriate monofunctionality may also be used, for example, 1-methylhexanoic acid or 4-hexenoic acid.

The linear and branched chain aliphatic monofunctional alcohols which may be used should be from about 2 to about 40 carbon atoms. Examples of such alcohols include methanol, ethanol, propanol, butanol, pentanol, hexanol and the like. The monofunctional hydroxyl group may be attached at any carbon site along the chain. Alkenyl, alkynyl, branched chain and nonaromatic cyclic alcohol derivatives of such straight chain alcohols having the appropriate monofunctionality may also be used, for example, propenol and similar alkenyl alcohols, isooctanol, 2-ethylhexanol, isodecanol, tridecanol and similar branched alcohols.

In addition to the foregoing, the monofunctional acids and alcohols may incorporate tertiary amine groups within the acid or alcohol chain.

Suitable primary and secondary amines which can be used for end-functionalizing the polyesters of the present invention include amines such as $XNH_2$ and $X_2NH$ where the X group is a branched or straight chain nonaromatic alkyl, alkenyl or alkynyl chain of from 2 to 40 carbon atoms which may be further amine substituted. The reaction of such a primary or secondary amine with polyesters of the present invention produces an amine functionalized polyester amide of formula (I) above, but with the $R^1$—H group, which is —OH or —O—$R^2$—OH, now being represented by —NHX or —$NX_2$ where X is a described above. Exemplary primary and secondary amines include dimethylaminopropylamine, diethylaminoethylamine, aminoethylethanolamine, monoethanolamine, diethanolamine, isopropanolamine, commercially available saturated normal amines having from 6 to 24 carbon atoms and saturated secondary amines.

Exemplary silicon-containing compounds include polysilicones and/or polysiloxanes. Preferred polysiloxanes have an —$Si(Y)_2O$— repeating unit where Y is a lower alkyl group of from 1–4 carbon atoms. Hydroxy-terminal polysiloxanes and monomeric silicon-containing species may also be used in the present invention.

In addition to the functionalized polyester, the organic formulations of the present invention include a first and a second organic active sunscreen ingredient. The organic active ingredients should be chosen such that the first ingredient is at least partially soluble in the second ingredient. If more than two ingredients are used, two of the ingredients should be at least partially soluble in at least one of the active ingredients. Further, the active ingredients should be selected such that they are compatible with and at least partially soluble in the functionalized polyester. When selecting a compatible polyester, it is preferred, based on this disclosure, that the solubility of the first ingredient in the second ingredient be increased by virtue of the functionalized polyester. That is, the combination of the first and second active ingredients with the functionalized polyester should exhibit a synergistic increase in the level of solubility of the first ingredient in the second ingredient as a result of combining the active ingredients with the functionalized polyester substantivity aid.

In addition, it is preferred that the polyester be partially soluble in the first and second ingredients, and more preferably, in the oil phase of the composition as a whole. By selecting active ingredients which are at least partially soluble in the active ingredients, the sunscreen formulation fixes the active ingredients within the functionalized polyester, which acts as a substantivity aid in the formulation. By using such a combination of components, the sunscreen formulation fixes and holds the active ingredients on the outer surface of the stratum corneum after applying the sunscreen to the skin, thereby decreasing the risks associated with daily penetration of active ingredients through the outer skin layers. In addition, the improved solubility levels significantly increase the resistance to wash-off of the formulation when the skin is immersed in water or due to perspiration. While it is preferred that the polyester be soluble in the active ingredients, it may also be dispersed in the active ingredients and still aid in the retention of the sunscreen active ingredients in the outer stratum corneum of the skin and in the improvement of the water-resistance of the sunscreen formulation.

In addition to the solubility properties as noted above, the organic active sunscreen ingredients should be capable of absorbing ultraviolet radiation in the UV-A and/or UV-B bands of the spectrum and considered safe and acceptable for use in a form suitable for topical application to the skin.

Exemplary organic active ingredients which have the above-characteristics and properties and which are suitable for use in practicing the present invention, include p-amino benzoic acid (PABA); glyceryl p-amino benzoate (glyceryl PABA or p-aminobenzoic acid monoglyceryl ester); ethyl-4-bis(hydroxypropyl)amino benzoate (ethyl dihydroxypropyl PABA); amyl para-dimethyl aminobenzoate (amyl dimethyl PABA); octyl dimethyl aminobenzoate (octyl dimethyl PABA, padimate O or 2-ethylhexyl dimethyl PABA); octyl salicylate (2-ethylhexyl salicylate); homosalate (HMS, homomenthyl salicylate or 3,3,5-trimethylcyclohexyl salicylate); triethanolamine salicylate (TEA salicylate); 2-ethoxyethyl-p-methoxycinnamate; diethanolamine-p-methoxycinnamate (DEA methoxycinnamate); octyl methoxycinnamate (OMC, octyl-p-methoxycinnamate or 2-ethylhexyl-p-methoxycinnamate); benzophenone-3 (oxybenzone); dioxybenzone (benzophenone-8); sulisobenzone (benzophenone-4); benzophenone-1; benzophenone-2; benzophenone-6; benzophenone-12; menthyl anthranilate; 2-ethylhexyl-2-cyano-3,3-diphenyl acrylate (octocrylene); 2-phenyl benzimidazole-5-sulfonic acid (phenylbenzimidazole sulfonic acid); digalloyl trioleate; 3-(4-methyl benzylidene)camphor; 4-isopropyl dibenzoyl methane; 2-ethyl-2-cyano-3,3'-diphenyl acrylate and avobenzone (butyl methoxydibenzoylmethane).

Preferred combinations of the first and second active sunscreen ingredients include benzophenone-3 and OMC or butyl methoxydibenzoylmethane (avobenzone) and OMC.

In addition to the functionalized polyester and the organic active sunscreen ingredients, the sunscreen formulations may also include standard inactive ingredients used in topical sunscreen preparations including carbomer 940, carbomer 941; preservatives such as methylparaben, propylparaben, sodium hydroxide solution and tetrasodium EDTA; emulsifiers and/or humectants such as triethanolamine, octyl stearate, glyceryl stearate, polyethylene glycol-100 stearate and propylene glycol; stabilizers such as cetyl alcohol, aluminum starch octylsuccinate; and emollients and/or emulsifiers such as isopropyl myristate, isopropyl palmitate, isopropyl stearate, cetearyl alcohol, ceteareth-20 and caprylic/capric triglyceride; stabilizers and/or thickeners such as hydroxyethylcellulose and acrylate polymers such as C10-30 alkyl acrylate crosspolymer. Other components, such as other inert ingredients, fragrances, stabilizers, emulsifiers, thickeners, humectants, colorants, further emollients, other film forming additives and preservatives, which will be known to those skilled in the art of sunscreen formulations and suitable for topical application may also be used.

In forming the sunscreen formulations according to the present invention, the formulations may be include a variety of base formulations such that the resulting formulation can be in the form of a solid, a gel, a cream, an emulsion, an oil or an aerosol. The limitations on the types of base formulations are dependent to a substantial extent upon the particular ingredients used in the formulation and their properties. The organic active sunscreen ingredients may be from about 1 to about 950 by weight of the entire formulation. Preferably, the organic active ingredients may be from about 1 to about 50% by weight, and more preferably, from about 1 to about 25% by weight of the composition. Similarly, the functionalized polyester may be from about 99 to about 5by weight of the entire formulation. More preferably, the polyester may be from about 10 to about 1% by weight of the entire formulation. It is possible, to provide a formulation which includes only the organic active sunscreen ingredients and the polyester, however, most commercial formulations would comprise a base formulation.

Further, any varied combination of two or more suitable organic active sunscreen ingredients meeting the solubility and other criteria noted above may be used in the formulation. However, it is preferred that the polyester component is about 1 to about 50 parts, more preferably about 1 to about 10 parts, by weight, of the formulation. The active sunscreen ingredients should collectively be about 50 to about 99 parts, more preferably about 50 to about 75 parts, by weight, of the formulation. The ratio of the organic active ingredients is preferably within a range in which the active ingredients are co-soluble with the polyester for varying amounts of the polyester within the formulation. Preferably, the organic active ingredients are not present in the formulation with the polyester in a dispersion or crystallized form, but are co-soluble and compatible with the polyester.

Figure 1:
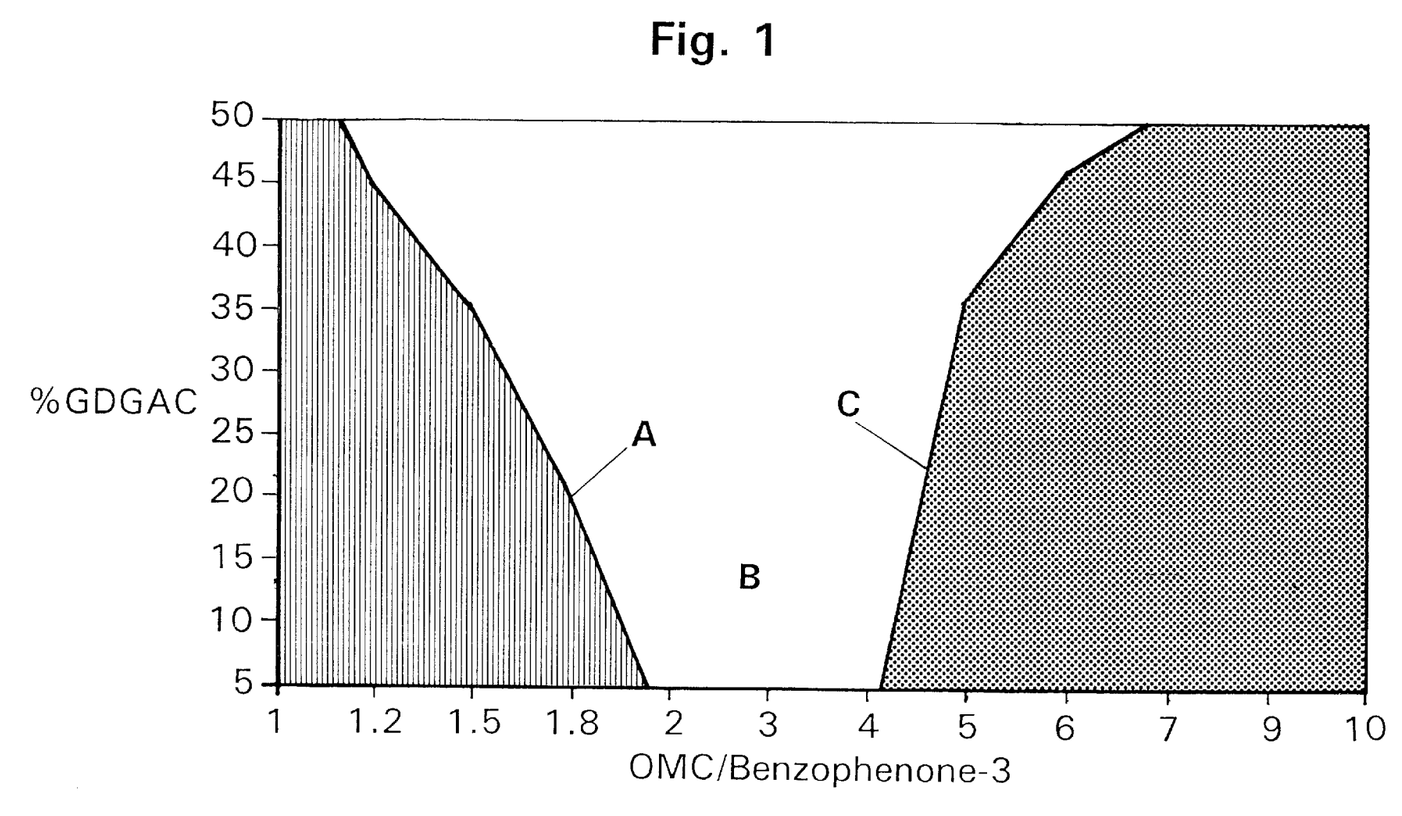
FIG. 1 is a graphical representation of the compatibility of glycerin/diethylene glycol/adipate crosspolymer with benzophenone-3 and octyl methoxycinnamate.

If the organic active ingredients used are benzophenone-3 and OMC, for example, in a formulation using GDGAC, the range of ratios of the parts by weight of benzophenone-3 to parts by weight of OMC to provide for an adequate solubility level is from about 1:8 to about 1:1. FIG. 1 graphically illustrates the inverse of these ratios (OMC/benzophenone- 3) for varying amounts of GDGAC. When the ratio of parts by weight of OMC/benzophenone-3 becomes too low (or the ratio of benzophenone-3/OMC becomes too high) as in Zone A, re-crystallization occurs. In Zone C, where the ratio of OMC/benzophenone-3 is too high (or the ratio of benzophenone-3/OMC is too low), dispersion occurs. As a result, the preferred formulation would include that range of ratios of organic active sunscreen ingredients in which co-solubility in the polyester substantivity aid can be maintained (Zone B). For GDGAC, excellent solubility levels of GDGAC in benzophenone-3 and OMC can be achieved for a wide range of ratios of those ingredients for up to about 45% by weight GDGAC.

An exemplary formulation according to the present invention which exhibits very water-resistant characteristics is shown below in Table 1. The formulation includes GDGAC as a functionalized polyester substantivity aid and ethylhexyl-p-methoxycinnamate (OMC), benzophenone-3 and 2-ethylhexyl salicylate (octyl salicylate) as organic active sunscreen ingredients.

TABLE 1

| Component Group | Component | Percent by Weight |
|---|---|---|
| A | deionized water | 72.24 |
|   | propylene glycol USP | 3.00 |
|   | methylparaben (LEXGARD ® M) | 0.20 |
|   | tetrasodium EDTA | 0.10 |
| B | ethylhexyl-p-methoxycinnamate | 7.50 |
|   | benzophenone-3 | 4.50 |
|   | GDGAC | 4.00 |
|   | cetearyl alcohol and ceteareth-20 (LEXEMUL ® CS-20) | 0.30 |
|   | glyceryl stearate (LEXEMUL ® 515) | 1.00 |
|   | octyl palmitate (LEXOL ® EHP) | 1.00 |
|   | 2-ethylhexyl salicylate | 5.00 |
|   | propylparaben (LEXGARD ® P) | 0.10 |
|   | acrylates/C10–30 alkyl acrylate crosspolymer | 0.40 |
| C | triethanolamine (99%) | 0.66 |

The method of the present invention includes a method for reducing the degree of penetration of an organic active sunscreen ingredient through an outer stratum corneum layer and for improving water resistance of a sunscreen formulation. The method includes providing to a sunscreen formulation having a first organic active sunscreen ingredient, a second active sunscreen ingredient and a functionalized polyester, such as those described above with respect to the sunscreen formulations of the present invention. The active ingredients may be those which are mentioned above and in which the first ingredient is at least partially soluble in the second ingredient. Preferably, the functionalized polyester is first prepared by reacting at least one aliphatic diol, at least one aliphatic diacid and up to about 10% by weight of at least one polyfunctional diol or alcohol as described above.

Typically, the reactants are charged to a vessel and heated to a temperature between about 120 to about 260° C., depending upon whether a catalyst is used. The reactants are held at pressures ranging from 40 psi to 1 mm Hg absolute. Heating is continued, depending upon the particular formulation, for a period of from about 10 to about 100 hours. Preferred reactions are carried out at a temperature of 220° C. with a starting pressure of 760 V which ramps as conversion proceeds to a pressure of 3 mm Hg absolute. The typical total reaction time is generally about 30 hours. Commercially available grades of reactants are used, and the reaction is generally carried out "neat" without addition of solvents.

As noted with respect to the formulations, the polyesters may be further functionalized by reacting them with linear or branched chain aliphatic monofunctional acids or alcohols of from about 2 to 40 carbon atoms, primary or secondary amines or silicon-containing compounds in the manner described above.

Preferably, the functionalized polyester used in the method is GDGAC as noted above and the active sunscreen ingredients are either benzophenone-3 and OMC or butyl methoxydibenzoylmethane and OMC.

In making a very water-resistant formulation according to the present invention, as exemplified above in Table 1, the components in Group A would be combined separately and heated to about 75°–80° C. while continuously mixing. The components in group B would be combined separately and heated to about 80°–85° C. while continuously mixing. Upon reaching homogeneity and their respective temperatures, the components of Groups A and B are combined by slowly adding the components in Group B to Group A. The mixture is then vigorously mixed for 5 minutes and then cooled. Mixing then continues at a speed no greater than the maximum possible speed which will not entrap air in the mixture. When the mixture is cooled to 50° C., the components of Group C are added to the mixture of A and B to form the final formulation. Mixing and cooling continue and, at 30°–35° C., the formulation is adjusted for water loss. The mixing and cooling continues until the temperature of the formulation is about 25°–30° C.

The invention will now be described in more detail with respect to the following specific, non-limiting examples:

EXAMPLE I

The solubility levels of benzophenone-3 in OMC were measured and are included in Table 2 below. In addition, the effect of GDGAC as a hydroxy-functionalized polyester on these two active ingredients was evaluated by providing GDGAC to combined benzophenone-3 and OMC at levels of 5% by weight and 45% by weight of the total formulation. As shown in Table 2, without GDGAC, benzophenone-3 is soluble in OMC up to about 20% by weight. Greater amounts of benzophenone-3 in OMC are crystalline. The percentage of benzophenone-3 which is soluble in OMC significantly increased to 35% by weight using only 5% GDGAC in the formulation. The solubility increased even more dramatically to a level of 45% when 45% by weight GDGAC was provided. This example illustrates the synergistic effect which occurs as a result of the combination of the functionalized polyester with two organic active ingredients.

TABLE 2

| % GDGAC in Solution | Percentage of Benzophenone-3 Soluble in OMC |
|---|---|
| 0 | 20 |
| 5 | 35 |
| 45 | 45 |

EXAMPLE II

Substantivity testing was performed on a GDGAC/OMC/benzophenone-3 formulation. The first substantivity tests were sensory testing using a panel of three people to determine the contribution of the GDGAC to the water-resistance of a skin lotion including the formulation. In this test, the panelists were asked to apply a lotion having the formulation listed in Table 3 below, including 2%. by weight GDGAC to the back of one hand.

The formulation of Table 3 was made by combining the ingredients in Component Group A, except for triethanolamine. The water was heated to 70° C., and mixed with a propeller mixer until all of the Carbomer was in solution. When the mixture became clear to translucent, the triethanolamine was added. In a separate vessel, the ingredients in Component Group B were combined and heated to 70° C. They were mixed at slow speed with a propeller mixer. The ingredients in Component Group B were slowly added to the ingredients in Component Group A with good agitation. The mixture was mixed at high speed for 5 minutes, and then the mixer speed was reduced to medium and cooling began. The batch was transferred to a homogenizer and the ingredients in Component Group C were added to the batch while homogenizing at medium speed. After 10 minutes of homogenization, the homogenizer was turned off and mixing continued using a propeller mixer. When the batch reached a temperature between 25° C. and 28° C., mixing was stopped and the formulation was adjusted for water loss.

A control formulation having no GDGAC was applied to the back of the other hand. Panelists were then asked to rinse both hands under running tap water and after their hands had dried, to report how much lotion they perceived as remaining on the back of each hand. The majority of the panelists, two out of three, reported a perceived level, after drying, of about 50% more lotion remaining on the hand having GDGAC. The majority of the panelists, two out of three, did not perceive any of the control lotion as remaining. A further panelist perception, on the average, was that the film deposited by the GDGAC-containing lotion had a moist, pleasant after-feeling.

TABLE 3

| Component Group | Component | Percent by Weight |
| --- | --- | --- |
| A | deionized water | 86.30 |
| | carbomer 941 | 0.30 |
| | methylparaben | 0.15 |
| | triethanolamine | 0.20 |
| B | octyl stearate | 7.50 |
| | glyceryl stearate and PEG-100 stearate | 3.50 |
| | propylparaben | 0.05 |
| C | GDGAC* | 2.00 |

*LEXOREZ ® 100

EXAMPLE III

Further substantivity testing was conducted using Horizontal Attenuated Total Reflectance Fourier Transform Infrared Spectrophotometry (FTIR) in order to quantitatively evaluate the relative presence of film on the surface of human skin in vivo. In the experiment, a series of sunscreen formulations were compared which varied only on the basis of the substantivity aid used, or the lack of a substantivity aid in the case of the control formulation. The base formulation used in shown below in Table 4. The substantivity aids tested and their reference number include GDGAC (LEXOREZ® 100) (1), polyvinylpyrrolidone (PVP)/hexadecene copolymer (2), dimethicone 350 cSt (3), PVP/Eicosene copolymer (4), acrylate/octylacrylamide copolymer (5) and tricontanyl PVP (6). Test formulations were applied to subjects' forearm skin in a dosage of approximately 2.5 mg of sample per $cm^2$. After the samples had dried, the sites were scanned with FTIR. The skin sites were then rinsed by pouring 250 ml of 30°–35° C. deionized water two times over the site and blotting with a paper towel after each rinse. After the skin sites were allowed to air-dry, they were again scanned with FTIR. The rinsing procedure was repeated followed by a third scan with FTIR. At the completion of the experiment, a series of three FTIR spectra were collected for each subject for each test formulation.

TABLE 4

| Component Group | Component | Percent By Weight |
| --- | --- | --- |
| A | water | 77.7 |
| | propylene glycol | 1.50 |
| | carbomer 940 | 0.30 |
| B | glyceryl stearate and polyethylene glycol-100 stearate | 4.00 |
| | glyceryl stearate | 1.00 |
| | cetyl alcohol | 0.50 |
| | aluminum starch octenylsuccinate | 1.00 |
| | caprylic/capric triglyceride | 3.00 |
| | isopropyl myristate and isopropyl palmitate and isopropyl stearate | 1.00 |
| | octyl methoxycinnamate | 8.00 |
| | SUBSTANTIVITY AID | 2.00 |
| C | sodium hydroxide solution | qs |

Each series of spectra showed the percentage of IR transmission within films formed on the skin sites following applications of the test formulations and within the film remaining on the skin following each successive rinse. The percentage change in transmission occurring between the application and the first rinse, between the first rinse and the second rinse and between the application and the second rinse were calculated for each series within the wavelength band of 3000 to 1680 cm $^{-1}$. The substantivity of each test formulation was compared based upon the relative increases in transmission which occurred following the first and second rinses. Larger increases in transmission corresponded to poorer skin substantivity. The base formulation used in the experiment was designed to deposit a significant amount of OMC on the skin and not contribute water-resistance except via the substantivity aid being compared. Following application and evaporation of bulk water, 30% or more of the formulation remaining on the skin was expected to consist of OMC.

In analyzing the spectra, two wavelength bands of significance were identified. The principal band extended from 3000 to 1680 $cm^{-1}$ which included the principle wavelengths in which OMC absorbs. It was also evident that within this band, percent transmission had significantly increased following successive rinses of the control formulation. This observation confirmed that the 3000 to 1680 $cm^{-1}$ band was characteristic of the film deposited on skin by the base formulation. The second band of interest was identified extending from 1650 to 1550 $cm^{-1}$. The change in transmission within the second band was generally inverse to the change in transmission within the 3000 to 1680 $cm^{-1}$ band. Amide bonds, as contained within polypeptides of stratum corneum keratin absorb within the 1650 to 1550 cm$^{-1}$ band. The decrease in percent transmission within the 1650 to 1550 cm$^{-1}$ band indicated that the test formulation was rinsed off, and the surface of the skin was detected by the FTIR. Due to the presence of ingredients within the base formulation which absorb within the 1550 to 1650 cm$^{-1}$ band, the change in transmission occurring in the first band was not directly proportional to transmission changes in the second band. In comparing the spectra collected during tests of the formulation containing GDGAC to the corresponding spectra collected in tests of the control formulation, the enhancement in water-resistance contributed by GDGAC was clearly demonstrated.

The results of the tests are shown in Table 5 below which summarizes the results for all formulations tested within the 3000 to 1680 cm$^{-1}$ band. As Table 5 clearly shows, the GDGAC formulation (1) exhibited the smallest increase in percent transmission following successive rinses. While the PVP hexadecene copolymer (2) performed comparably following the first rinse, after the second rinse, almost twice the amount of the PVP hexadecene copolymer formulation was rinsed off in comparison with the GDGAC formulation.

TABLE 5

| Substantiv-ity Aid | % Change in Transmission: Application to First Rinse | % Change in Transmission: First Rinse to Second Rinse | % Change in Transmission: Application to Second Rinse |
|---|---|---|---|
| 1 | 48 | 19 | 58 |
| 2 | 51 | 35 | 69 |
| 3 | 69 | 19 | 75 |
| 4 | 71 | 35 | 81 |
| 5 | 76 | 38 | 85 |
| 6 | 80 | 40 | 88 |
| Control | 80 | 52 | 90 |

EXAMPLE IV

To evaluate the impact of the functionalized polyester on skin penetration of organic active sunscreen ingredients, a series of "tape stripping" experiments using GDGAC were conducted on human skin in vivo. In these experiments, solutions of organic active sunscreen ingredients, with and without GDGAC, were applied to sites on the forearm skin of subjects. Following a period of sample residence time of up to two hours, the outer stratum corneum was removed via repeated tape stripping. Following the recovery process, the tape strips were immersed in tetrahydrofuran to separate the tape backing. After the samples were separated from the tape backing and were in solution, 2 μl were injected into a gas chromatograph (GC) equipped with a mass selective detector. Peak identification and quantification were conducted using an external standard for OMC and benzophenone-3. The percentage of each active ingredient recovered was calculated for individual tape strips based on the percent of the respective actives contained in the test solutions and the dosage of test solution applied to the site.

Table 6 shows the results of a two-hour residence time study involving OMC and benzophenone-3. In this study, three test solutions were applied which contained a ratio of 3 parts by weight benzophenone-3 to 7 parts OMC (a ratio of 1:2.3). Test solution dosages were in the range of from 2.3 to 3.3 mg of sample/cm$^2$. One test solution consisted of the two actives neat. The second solution contained 25% GDGAC and the third contained 25% of a copolymer including poly[oxy(methyl-1,2-ethanediyl)], α-hydro-ω-hydroxy polymer with 1,1'-methylene-bis-[4-isocyanatocyclohexane] otherwise known as PPG-12/SMDI copolymer. Prior to application of the test solutions, skin sites were perturbed by tape stripping each site three times. After two hours, the outer stratum corneum of each test site was recovered by tape stripping three times. For analysis purposes, the results obtained from individual tape strips were combined for each skin site. Table 6 summarizes the results obtained in recovery of OMC. When the two active ingredients were applied neat, about 56% of the applied OMC was recovered. About 65% of the applied OMC was recovered when the active ingredients were applied in combination with 25% PPG-12/SMDI copolymer. When 25% GDGAC was used, greater than 90% of the applied OMC was recovered. Table 6 also shows the results of the recovery of benzophenone-3. The error in the benzophenone-3 data is somewhat larger than for the recovery of OMC due to the smaller amount of benzophenone-3 used and recovered. Even with the greater percentage error in the benzophenone-3 data, on the average, only 20% of the applied benzophenone-3 was recovered when the active ingredients were applied neat, 65% of the applied benzophenone-3 was recovered when the active ingredients were applied with 25% PPG-12/SMDI copolymer and greater than 90% of the applied benzophenone-3 was recovered when 25% GDGAC was used.

TABLE 6

| Formulation | % OMC Recovered | % Benzophenone-3 Recovered |
|---|---|---|
| OMC and Benzophenone-3 | 56 | 20 |
| OMC; Benzophenone-3 and PPG-12/SMDI Copolymer | 65 | 65 |
| OMC; Benzophenone-3 and GDGAC | >90 | >90 |

EXAMPLE V

Although the protocol required by the U.S. Food and Drug Administration for rating waterproof (or very water-resistant) performance of various products specifies 80 minutes of water immersion, many marketers are interested in all day (8-hour) water-resistance. In the 8-hour immersion protocol, two skin sites on subjects' backs were dosed with test formulations and one site was dosed with a homosalate standard solution. Immediately after application, the homosalate-treated site and one site treated with test formulation were irradiated. After eight hours of immersion in a whirlpool bath, the second site treated with the test formulation was irradiated. The relative degree of erythema visible in the two sites dosed with the test formulation were graded in reference to the erythema visible in the homosalate treated site. For each formulation tested, an average SPF was calculated for sites irradiated before and after 8 hours of immersion (pre- and post-immersion). The formulation of Table 7 below is the sunscreen base formulation used in the test. Three variations were prepared. One variation was the control formulation which included no substantivity aid. The second variation contained 3% GDGAC. The third variation contained 3% PPG-12/SMDI copolymer. In order to test only the effect of the substantivity aids, the base formulation was designed to minimize its contribution to water-resistance.

TABLE 7

| Component Group | Component | Percent by Weight |
|---|---|---|
| A | water | 61.60 |
| | propylene glycol | 3.00 |
| | hydroxyethylcellulose | 0.40 |
| B | glyceryl stearate and polyethylene glycol-100 stearate | 3.00 |
| | glyceryl stearate | 3.00 |
| | OMC | 7.50 |
| | benzophenone-3 | 6.00 |
| | 2-ethylhexyl salicylate | 5.00 |
| | padimate O | 5.00 |
| | octyl palmitate | 3.00 |
| | SUBSTANTIVITY AID | 3.00 |

The SPF tests reported here were conducted by Consumer Product Testing Co., Inc. of Fairfield, N.J. The results of the SPF testing are included in Table 8 below.

TABLE 8

| Substantivity Aid | Average Pre-Immersion SPF | Average Post-Immersion SPF (after 8 hours) |
|---|---|---|
| GDGAC (3%) | 22 | 12 |
| PPG-12/SMDI copolymer (3%) | 23 | 12 |
| Control (no substantivity aid) | 20 | 9 |

The results show that the formulation having 3% GDGAC exhibited an average pre-immersion SPF of 22 and an average post-immersion SPF of 12. The formulation having 3% PPG-12/SMDI copolymer had a slightly higher average SPF of 23 pre-immersion, but exhibited the same average post-immersion SPF as the GDGAC-containing formulation. The control exhibited a significantly lower average pre-immersion and post-immersion SPF than either formulation containing substantivity aids. The pre-immersion SPF of 20 exhibited by the control suggests that both substantivity aids tested improved static SPF, by coupling the active ingredients into a more homogeneous phase or contributing to a thicker applied film. Based upon the average post-immersion SPF of the control formulation, an SPF of 9, both substantivity aids improved post-immersion SPF by 33%. Since the based formulation was not water-resistant, other than through inclusion of 3% of a substantivity aid, the 33% improvement in post-immersion performance was significant.

A higher level of substantivity aids in conjunction with a redesigned base formula would be necessary to achieve higher degrees of water-resistance over eight hours. Another useful formulation strategy includes use of an emulsification system with greater resistance to re-emulsification following water-immersion, for example, a preferred very water-resistant formulation according to the present invention as shown above in Table 1.

EXAMPLE VI

Occlusive films applied to skin are known to interfere with transepidermal water loss, resulting in increased epidermal moisture immediately beneath the film. Topical skin preparations which form occlusive films also tend to contribute a sensation of warmth and discomfort. The relative occlusivity of the functionalized polyesters used in the present invention was demonstrated by an experiment using GDGAC. The relative change in skin surface capacitance was determined for untreated human skin sites, sites treated with GDGAC and sites treated with petrolatum. Petrolatum is known to be relatively high in occlusivity. The electrical properties of the skin are related to relative moisture content. The realtive moisture content of the skin can be indexed either as electrical potential or resistance to current flow. As such, skin surface capacitance was measured using a NOVA DPM Moisture Meter. The NOVA meter records skin surface capacitance as DPM values. The DPM values are directly related to capacitance of the outer stratum corneum of the skin. DPM measurements correlate to relative units of skin moiturization. Therefore, increases in DPM values can be correlated with increases in epidermal moisture. In the experiment, treated and untreated sites were monitored with the NOVA meter over a 14 minute period. The results are shown in Table 9 below.

TABLE 9

| Skin Treatment | Average % Increase in DPM Values |
|---|---|
| untreated skin | 0% |
| skin treated with GDGAC | 5% |
| skin treated with petrolatum | 45% |

The skin site treated with petrolatum exhibited a 45% average increase in DPM values. The untreated skin site showed no average increase. The GDGAC-treated site showed only a 5% average increase in DPM values indicating that GDGAC would not be considered occlusive.

The invention also includes a sunscreen formulation including a dispersion of an inorganic active sunscreen ingredient in a functionalized polyester. The functionalized polyesters which may be used include those described above with respect to the organic active-based formulations. The functionalized polyesters act as a dispersing aid for inorganic active sunscreen ingredients. Suitable inorganic active ingredients which may be used in these formulations include titanium dioxide, zinc oxide, and iron oxides. Preferably, each of these inorganic oxides is used with the polyesters of the invention as described above in a range of ratios of from about 0.1:1 to about 10:1, more preferably from about 1:1 to 5:1 of the inorganic oxide to the polyester.

The inorganic active sunscreen ingredients can be used effectively with the polyesters of the present invention by combining the active ingredients in the oil phase of a sunscreen formulation along with the polyester. Preferably, after all of the components of the oil phase have been combined, the inorganic particles are dispersed via either homogenization, colloid milling or grinding in a three roller ointment mill in a manner which would be understood by one skilled in the art.

The invention will now be described with respect to further, non-limiting examples as follows:

EXAMPLE VII

An experiment was conducted in which micronized zinc oxide was dispersed in anhydrous solutions with and without the functionalized polyester as a dispersing aid. The test formulation is shown below in Table 10. Samples of the test solutions were stored for 30 days in test tubes under ambient conditions and then examined to determine the relative concentration of zinc oxide particles remaining in suspension. After 30 days, some zinc oxide had settled to the bottom of all test solutions. All zinc oxide appeared to have settled to the bottom of the control solution which contained no dispersing aid. A small amount of each test solution was drawn from the top of each test tube containing dispersed zinc oxide and photographed through a light microscope at 135× magnification. Photomicrographs of the three test solutions including the different dispersing aids were examined. In the photomicrographs, the specks represented zinc oxide particles remaining in the dispersion. Based on the relative concentration of zinc oxide particles in the photomicrographs, the effectiveness of GDGAC as a dispersing aid appeared roughly equivalent to PVP hexadecene copolymer. All of the test solutions appeared significantly more effective than the control solution. The results of this experiment show the effectiveness of the functionalized polyesters as dispersing aids for inorganic active sunscreen ingredients.

In view of the foregoing, the present invention represents a significant breakthrough in the sunscreen area by providing sunscreen formulations which allow for use of high SPF value organic active sunscreen ingredients, but which protect the daily user from absorption of such ingredients through the stratum corneum. The formulations also provide excellent resistance to wash-off from water immersion or perspiration such that protection from UV-A and UV-B rays can be extended over a significant length of time without reapplication. The formulations are not occlusive to human skin. Further, the functionalized polyesters which serve as excellent substantivity aids for the organic active sunscreen ingredients also function well as dispersing agents for inorganic active sunscreen ingredients.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sunscreen formulation, comprising:
   (a) a functionalized polyester which is a reaction product of at least one diol, at least one diacid and which has a functionality of at least 2;
   (b) a first organic active sunscreen ingredient; and
   (c) a second organic active sunscreen ingredient, wherein the first ingredient is at least partially soluble in the second active ingredient and wherein the first and second active ingredients are at least partially soluble in the functionalized polyester.

2. The sunscreen formulation according to claim 1, wherein the polyester is a reaction product of at least one diol, at least one diacid and at least one polyfunctional alcohol or polyfunctional acid present in an amount up to 10% by weight.

3. The sunscreen formulation according to claim 2, wherein the polyester is glycerin/diethylene glycol/adipate crosspolymer.

4. The sunscreen formulation according to claim 2, wherein the polyester is further end-functionalized by at least one compound selected from the group consisting of linear and branched chain aliphatic monofunctional acids having from about 2 to 40 carbon atoms, linear and branched chain aliphatic monofunctional alcohols having from 2 to 40 carbon atoms, primary amines, secondary amines, and silicon-containing compounds.

5. The sunscreen formulation according to claim 1, wherein the number average molecular weight of the polyester is from about 500 to about 20,000.

6. The sunscreen formulation according to claim 1, wherein the first ingredient is benzophenone-3 and the second ingredient is octyl methoxycinnamate.

7. The sunscreen formulation according to claim 6, wherein the formulation comprises from about 1 to about 50 parts by weight of the polyester and from about 50 to about 99 parts by weight combined of the benzophenone-3 and the octyl methoxycinnamate.

8. The sunscreen formulation according to claim 7, wherein a ratio of parts by weight of the benzophenone-3 to parts by weight of the octyl methoxycinnamate in the sunscreen formulation is from about 1:8 to about 1:1.

9. The sunscreen formulation according to claim 1, wherein the first ingredient is butyl methoxydibenzoylmethane and the second ingredient is octyl methoxycinnamate.

10. A sunscreen formulation, comprising:
    (a) from about 1 to about 50 parts by weight of a functionalized polyester, wherein the polyester is a reaction product of at least one diol, at least one diacid and at least one polyfunctional alcohol or polyfunctional acid present in an amount up to 10% by weight and sufficient to provide a minimum functionality of at least 2; and
    (b) from about 50 to about 99 parts by weight combined of a first organic active sunscreen ingredient and a second organic active sunscreen ingredient, wherein the first ingredient is at least partially soluble in the second ingredient in the formulation.

11. The sunscreen formulation according to claim 10, wherein the polyester is glycerin/diethylene glycol/adipate crosspolymer.

12. The sunscreen formulation according to claim 10, wherein the first ingredient is benzophenone-3 and the second ingredient is octyl methoxycinnamate.

13. The sunscreen formulation according to claim 12, wherein a ratio of parts by weight of the benzophenone-3 to parts by weight of the octyl methoxycinnamate in the sunscreen formulation is from about 1:8 to about 1:1.

14. A method for reducing the degree of penetration of an organic active sunscreen ingredient through an outer stratum corneum layer and for improving water resistance of a sunscreen formulation having a first organic active sunscreen ingredient, comprising providing to the sunscreen formulation a second organic active sunscreen ingredient and a functionalized polyester which is a reaction product of at least one diol, at least one diacid and which has a functionality of at least 2, wherein the first ingredient is at least partially soluble in the second ingredient in the formulation and wherein the first and second active ingredients are at least partially soluble in the functionalized polyester.

15. The method according to claim 14, wherein the functionalized polyester is the reaction product of at least one aliphatic diol, at least one aliphatic diacid and at least one polyfunctional alcohol or polyfunctional acid present in an amount up to 10% by weight and sufficient to provide a minimum functionality of at least 2 in the functionalized polyester.

16. The method according to claim 15, wherein the functionalized polyester is a glycerin/diethylene glycol/adipate crosspolymer.

17. The method according to claim 15, wherein the polyester is further end-functionalized by at least one compound selected from the group consisting of linear and branched chain aliphatic monofunctional acids having from about 2 to 40 carbon atoms, linear and branched chain aliphatic monofunctional alcohols having from 2 to 40 carbon atoms, primary amines, secondary amines, and silicon-containing compounds.

18. The method according to claim 14, wherein the first active ingredient is benzophenone-3 and the second active ingredient is octyl methoxycinnamate.

19. The method according to claim 14, wherein the first ingredient is butyl methoxydibenzoylmethane and the second ingredient is octyl methoxycinnamate.

20. In a method for reducing the degree of penetration of an organic active sunscreen ingredient through an outer stratum corneum layer and for improving the water resistance of a sunscreen formulation comprised of a polyester and at least one organic active sunscreen ingredient, the improvement comprising providing a glycerin/diethylene glycol/adipate crosspolymer as the polyester and octyl methoxycinnamate and benzophenone-3 as the at least one organic active sunscreen ingredient, wherein a ratio of parts by weight of the benzophenone-3 to parts by weight of the octyl methoxycinnamate in the sunscreen formulation is from about 1:8 to about 1:1.

21. A sunscreen formulation, comprising a dispersion of an inorganic active sunscreen ingredient in a functionalized polyester.

* * * * *